(12) United States Patent
Rao et al.

(10) Patent No.: US 7,994,220 B2
(45) Date of Patent: Aug. 9, 2011

(54) MILNACIPRAN FOR THE LONG-TERM TREATMENT OF FIBROMYALGIA SYNDROME

(75) Inventors: Srinivas G. Rao, Encinitas, CA (US); Michael Gendreau, Poway, CA (US); Jay D. Kranzler, La Jolla, CA (US)

(73) Assignee: Cypress Bioscience, Inc., San Diego, CA (US)

( * ) Notice: Subject to any disclaimer, the term of this patent is extended or adjusted under 35 U.S.C. 154(b) by 1089 days.

(21) Appl. No.: 11/535,237

(22) Filed: Sep. 26, 2006

(65) Prior Publication Data

US 2007/0072946 A1 Mar. 29, 2007

Related U.S. Application Data

(60) Provisional application No. 60/721,722, filed on Sep. 28, 2005.

(51) Int. Cl.
*A61K 31/16* (2006.01)
*A61K 31/015* (2006.01)
(52) U.S. Cl. ...................................... 514/579; 514/765
(58) Field of Classification Search .................. 514/579, 514/765
See application file for complete search history.

(56) References Cited

U.S. PATENT DOCUMENTS

| | | |
|---|---|---|
| 3,652,589 A | 3/1972 | Flick et al. |
| 4,177,290 A | 12/1979 | Lafon |
| 4,478,836 A | 10/1984 | Mouzin et al. |
| 4,708,834 A | 11/1987 | Cohen |
| 4,710,384 A | 12/1987 | Rotman |
| 4,734,285 A | 3/1988 | Alderman |
| 4,740,198 A | 4/1988 | Theeuwes |
| 4,756,911 A | 7/1988 | Drost et al. |
| 4,761,501 A | 8/1988 | Husbands et al. |
| 4,775,535 A | 10/1988 | Lowey |
| 4,781,919 A | 11/1988 | Liebowitz |
| 4,784,858 A | 11/1988 | Ventouras |
| 4,792,448 A | 12/1988 | Ranade |
| 4,795,327 A | 1/1989 | Gaylord et al. |
| 4,795,642 A | 1/1989 | Cohen et al. |
| 4,795,645 A | 1/1989 | Friedman et al. |
| 4,798,725 A | 1/1989 | Patel |
| 4,800,083 A | 1/1989 | Hom et al. |
| 4,803,076 A | 2/1989 | Ranade |
| 4,803,079 A | 2/1989 | Hsiao et al. |
| 4,806,359 A | 2/1989 | Radebaugh et al. |
| 4,816,262 A | 3/1989 | McMullen |
| 4,820,522 A | 4/1989 | Radebaugh et al. |
| 4,822,619 A | 4/1989 | Eichel et al. |
| 4,824,678 A | 4/1989 | Lindahl et al. |
| 4,832,957 A | 5/1989 | Dempski et al. |
| 4,837,032 A | 6/1989 | Ortega |
| 4,839,177 A | 6/1989 | Colombo et al. |
| 4,842,866 A | 6/1989 | Horder et al. |
| 4,849,229 A | 7/1989 | Gaylord et al. |
| 4,861,590 A | 8/1989 | Grodberg |
| 4,863,743 A | 9/1989 | Hsiao et al. |
| 4,871,548 A | 10/1989 | Edgren et al. |
| 4,882,167 A | 11/1989 | Jang |
| 4,886,812 A | 12/1989 | Griss et al. |
| 4,891,233 A | 1/1990 | Belanger et al. |
| 4,892,742 A | 1/1990 | Shah |
| 4,956,388 A | 9/1990 | Robertson et al. |
| 5,034,541 A | 7/1991 | Bigg et al. |
| 5,397,574 A | 3/1995 | Chen |
| 5,399,359 A | 3/1995 | Baichwal |
| 5,399,362 A | 3/1995 | Baichwal et al. |
| 5,419,917 A | 5/1995 | Chen et al. |
| 5,422,123 A | 6/1995 | Conte et al. |
| 5,456,921 A | 10/1995 | Mateescu et al. |
| 5,458,005 A | 10/1995 | Perelsteyn |
| 5,458,887 A | 10/1995 | Chen et al. |
| 5,458,888 A | 10/1995 | Chen |
| 5,464,633 A | 11/1995 | Conte et al. |
| 5,472,708 A | 12/1995 | Chen |
| 5,512,297 A | 4/1996 | Baichwal |
| 5,532,244 A | 7/1996 | Wong et al. |
| 5,532,250 A | 7/1996 | Wong et al. |
| 5,532,268 A | 7/1996 | Wong et al. |
| 5,603,956 A | 2/1997 | Mateescu et al. |
| 5,621,142 A | 4/1997 | Mochizuki et al. |
| 5,658,955 A | 8/1997 | Hitzig |
| 5,725,883 A | 3/1998 | Staniforth et al. |
| 5,744,474 A | 4/1998 | Thor |
| 5,773,025 A | 6/1998 | Baichwal |
| 5,776,969 A | 7/1998 | James |
| 5,792,796 A | 8/1998 | Woodruff et al. |
| 5,824,638 A | 10/1998 | Burnside et al. |
| 5,834,023 A | 11/1998 | Chen |
| 5,837,379 A | 11/1998 | Chen et al. |
| 5,885,616 A | 3/1999 | Hsiao et al. |
| 5,897,876 A | 4/1999 | Rudnic et al. |
| 5,912,013 A | 6/1999 | Rudnic et al. |
| 5,912,256 A | 6/1999 | Koch et al. |
| 5,916,595 A | 6/1999 | Chen et al. |
| 5,942,549 A | 8/1999 | Vargas |
| 5,945,416 A | 8/1999 | Shannon et al. |

(Continued)

FOREIGN PATENT DOCUMENTS

CA 2431041 7/2002

(Continued)

OTHER PUBLICATIONS

Anderberg et al, European Journal of Pain 2000; 4(1):27-35.

(Continued)

*Primary Examiner* — Sreeni Padmanabhan
*Assistant Examiner* — Renee Claytor
(74) *Attorney, Agent, or Firm* — Finnegan, Henderson, Farabow, Garrett & Dunner, LLP

(57) ABSTRACT

The present invention is directed to methods for providing long-term treatment of fibromyalgia syndrome (FMS) by administering a dual re-uptake inhibitor to a patient with FMS. More particularly, the present invention is directed to the long-term treatment of FMS by administering a norepinephrine-serotonin reuptake inhibitor (NSRI) to a patient with FMS.

7 Claims, 2 Drawing Sheets

U.S. PATENT DOCUMENTS

| | | | |
|---|---|---|---|
| 5,952,004 | A | 9/1999 | Rudnic et al. |
| 5,994,363 | A | 11/1999 | El-Rashidy et al. |
| 6,004,582 | A | 12/1999 | Faour et al. |
| 6,028,070 | A | 2/2000 | Heiligenstein |
| 6,066,643 | A | 5/2000 | Perry |
| 6,077,541 | A | 6/2000 | Chen et al. |
| 6,096,340 | A | 8/2000 | Chen et al. |
| 6,099,859 | A | 8/2000 | Cheng et al. |
| 6,099,862 | A | 8/2000 | Chen et al. |
| 6,103,263 | A | 8/2000 | Lee et al. |
| 6,106,862 | A | 8/2000 | Chen et al. |
| 6,110,498 | A | 8/2000 | Rudnic et al. |
| 6,184,222 | B1 | 2/2001 | Heiligenstein |
| 6,380,200 | B1 | 4/2002 | Mylari |
| 6,395,788 | B1 | 5/2002 | Iglehart, III |
| 6,432,989 | B1 | 8/2002 | Chen |
| 6,441,038 | B1 | 8/2002 | Loder et al. |
| 6,451,788 | B1 | 9/2002 | Horrobin et al. |
| 6,489,341 | B1 | 12/2002 | Jerussi |
| 6,500,853 | B1 | 12/2002 | Seehra et al. |
| 6,596,900 | B2 | 7/2003 | Blakemore et al. |
| 6,602,911 | B2 | 8/2003 | Kranzler et al. |
| 6,635,675 | B2 | 10/2003 | Kranzler et al. |
| 6,964,962 | B2 | 11/2005 | Wong et al. |
| 6,992,110 | B2 | 1/2006 | Kranzler et al. |
| 7,005,452 | B2 | 2/2006 | Deregnaucourt et al. |
| 7,888,342 | B2 | 2/2011 | Kranzler et al. |
| 2001/0036943 | A1 | 11/2001 | Coe et al. |
| 2002/0006963 | A1 | 1/2002 | Young et al. |
| 2002/0010216 | A1 | 1/2002 | Rogosky et al. |
| 2002/0086864 | A1 | 7/2002 | Wong et al. |
| 2002/0094986 | A1 | 7/2002 | Chappell et al. |
| 2002/0147196 | A1 | 10/2002 | Quessy et al. |
| 2002/0156267 | A1 | 10/2002 | Shukla et al. |
| 2002/0187958 | A1 | 12/2002 | Horrobin et al. |
| 2003/0013689 | A1 | 1/2003 | Helton et al. |
| 2003/0082214 | A1 | 5/2003 | Williams et al. |
| 2003/0082225 | A1 | 5/2003 | Mason |
| 2003/0130353 | A1 | 7/2003 | Kranzler et al. |
| 2003/0143548 | A1 | 7/2003 | Camilleri et al. |
| 2003/0203055 | A1 | 10/2003 | Rao et al. |
| 2003/0232805 | A1 | 12/2003 | Kranzler et al. |
| 2004/0014739 | A1 | 1/2004 | Kopple |
| 2004/0019116 | A1 | 1/2004 | Kranzler et al. |
| 2004/0034101 | A1 | 2/2004 | Rao et al. |
| 2004/0063628 | A1 | 4/2004 | Piccariello et al. |
| 2004/0106681 | A1 | 6/2004 | Rao et al. |
| 2004/0132826 | A1 | 7/2004 | Hirsh et al. |
| 2004/0228830 | A1 | 11/2004 | Hirsh et al. |
| 2004/0229956 | A1 | 11/2004 | Kranzler et al. |
| 2005/0014843 | A1 | 1/2005 | Allen et al. |
| 2005/0032782 | A1 | 2/2005 | Rao et al. |
| 2005/0096395 | A1 | 5/2005 | Rao et al. |
| 2006/0024366 | A1 | 2/2006 | Hirsh et al. |
| 2007/0225375 | A1 | 9/2007 | Kranzler et al. |
| 2008/0034101 | A1 | 2/2008 | Tran et al. |
| 2008/0058317 | A1 | 3/2008 | Rao et al. |
| 2008/0058318 | A1 | 3/2008 | Rao et al. |
| 2008/0153919 | A1 | 6/2008 | Kranzler et al. |
| 2008/0293820 | A1 | 11/2008 | Rao et al. |
| 2010/0105779 | A1 | 4/2010 | Kranzler et al. |
| 2010/0197796 | A1 | 8/2010 | Kranzler et al. |

FOREIGN PATENT DOCUMENTS

| | | |
|---|---|---|
| EP | 0 759 299 | 2/1997 |
| EP | 0 814 084 | 12/1997 |
| EP | 0 818 198 | 1/1998 |
| FR | 2 752 732 | 3/1998 |
| GB | 2 362 826 | 12/2001 |
| RU | 2187307 C1 | 8/2002 |
| WO | WO 94/00114 | 1/1994 |
| WO | WO 95/22521 | 8/1995 |
| WO | WO 97/10816 | 3/1997 |
| WO | WO 97/33880 | 9/1997 |
| WO | WO 97/35574 | 10/1997 |
| WO | WO 97/35584 | 3/1998 |
| WO | WO 98/08495 | 3/1998 |
| WO | WO 98/36744 | 8/1998 |
| WO | WO 98/47491 | 10/1998 |
| WO | WO 99/15176 | 4/1999 |
| WO | WO 00/10551 | 3/2000 |
| WO | WO 00/15223 | 3/2000 |
| WO | WO 00/32178 | 6/2000 |
| WO | WO 00/56310 | 9/2000 |
| WO | WO 00/56318 | 9/2000 |
| WO | WO 00/76956 | 12/2000 |
| WO | WO 01/26623 | 4/2001 |
| WO | WO 01/38293 | 5/2001 |
| WO | WO 02/053140 | 7/2002 |
| WO | WO 03/039598 | 5/2003 |
| WO | WO 03/053426 | 7/2003 |
| WO | WO 03/068211 | 8/2003 |
| WO | WO 2004/009069 | 1/2004 |
| WO | WO 2004/030633 | 4/2004 |
| WO | WO 2004/045718 | 6/2004 |
| WO | WO 2007/038620 | 4/2007 |
| WO | WO 2008/019388 | 2/2008 |
| WO | WO 2008/021932 | 2/2008 |
| WO | WO 2008/147843 | 12/2008 |

OTHER PUBLICATIONS

Bennett R, Journal of Functional Syndromes 2001; 1(1):79-92.
Buskila D., Bailliere's Best Practice & Research Clinical Rheumatology 1999; Vol. 13, No. 3, pp. 479-485.
Carette et al., Arthritis & Rheumatism 1994; 37(1):32-40.
Clauw DJ and Chrousos GP, Neuroimmunomodulation 1997;4(3):134-153.
Dwight et al., Psychosomatics 1998;39(1)14-17.
Goldenberg et al., Arthritis & Rheumatism 1996;39(11)1862-1859.
Lautenschlager J, Scand J Rheumatol Suppl. 2000:113:32-36.
Leventhal LJ, Ann Intern Med, 1999;131:850-858.
Norregaard et al, Pain 1995;61(3):445-449.
Sindrup SH and Jensen TS, Pain 1999;83(3):389-400.
Wolfe, at al., Arthritis Rheum. 1990;33(2)160-172.
Wolfe et al., Scand J Rheum. 1994;23(5):255-259.
Wolfe at al., Arthritis Rheum. 1995;38(1):19-28.
Wolfe et al., Arthritis Rheum. 1997;40(9):1571-1579.
Fuller, Clinical Applications of 5-HT Uptake Inhibitors, Advances in the Biosciences, vol. 85, pp. 255-270, 1992.
Lecrubier, Milnacipran: The Clinical Properties of a Selective Serotonin and Noradrenaline Reuptake Inhibitor (SNRI), Human Psychopharmacol. Clin., vol. 12, pp. S127-S134, 1997.
Farthing, New Drugs in the Management of the Irritable Bowel Syndrome, Drugs, vol. 56, pp. 11-21, 1998.
O'Malley, et al., Treatment of Fibromyalgia with Antidepressants, J. Gen. Intern. Med., vol. 15, pp. 659-666, 2000.
Mertz, Irritable Bowel Syndrome, N. Engl. J. Med., vol. 349(22), pp. 2136-2146, 2003.
Fennerty, Traditional Therapies for Irritable Bowel Syndrome: An Evidence-Based Appraisal, Rev. Gastroenterol. Disord., vol. 3, Suppl. 2, pp. 18-24, 2003.
Patel, et al., The Placebo Effect in Irritable Bowel Syndrome Trials: A Meta-Analysis, Neurogastroenterol. Motil., vol. 17, pp. 332-340, 2005.
Patient Information Leaflet: Ixel 25 mg, hard capsule; Feb. 2003.
Patient Information Leaflet: Ixel 50 mg, hard capsule; Feb. 2003.
Patient Information Leaflet: Toledomin Tablets 15, Toledomin Tablets 25; Nov. 2003.
Advisory Action dated May 12, 2008, in U.S. Appl. No. 10/678,767, filed Oct. 3, 2003.
Advisory Action dated Dec. 24, 2008, in U.S. Appl. No. 10/623,431, filed Jul. 18, 2003.
Amendment Accompanying Request for Continued Examination dated May 27, 2007, in U.S. Appl. No. 10/623,431, filed Jul. 18, 2003.
Amendment Accompanying Request for Continued Examination dated Sep. 3, 2009, in U.S. Appl. No. 10/678,767, filed Oct. 3, 2003.
Amendment and Response dated Apr. 6, 2009, in U.S. Appl. No. 11/835,620, filed Aug. 8, 2007.
Amendment and Response dated Mar. 18, 2009, in U.S. Appl. No. 11/835,590, filed Aug. 8, 2007.
Amendment and Response to Office Action dated Jun. 17, 2009, in U.S. Appl. No. 11/752,213, filed May 22, 2007.

Amendment and Response to Office Action dated Oct. 21, 2008, in U.S. Appl. No. 12/035,820, filed Feb. 22, 2008.
Amendment and Response to Office Action dated Aug. 2, 2007, in U.S. Appl. No. 10/628,141, filed Jul. 24, 2003.
Amendment and Response to Office Action dated Jan. 3, 2007, in U.S. Appl. No. 10/628,141, filed Jul. 24, 2003.
Amendment and Response to Office Action dated Aug. 31, 2006, in U.S. Appl. No. 10/628,141, filed Jul. 24, 2003.
Amendment and Response to Office Action dated Feb. 28, 2006, in U.S. Appl. No. 10/628,141, filed Jul. 24, 2003.
Amendment and Response to Restriction Requirement and Applicant Statement of Interview Summary dated Jun. 17, 2009, issued in U.S. Appl. No. 12/035,820, filed Feb. 22, 2008.
Amendment dated May 7, 2004, in European Application No. 02793880.2.
Applicant Statement of Interview Summary dated May 7, 2009, issued in U.S. Appl. No. 11/752,213, filed May 22, 2007.
Communication pursuant to Article 94(3) EPC dated Dec. 17, 2007, in European Application No. 02793880.2.
Communication pursuant to Article 96(2) EPC dated Jun. 1, 2005, in European Application No. 02793880.2.
European Office Action for European Application No. 03748971.3, dated Oct. 25, 2006.
Examiner's first report dated Mar. 5, 2008 in Australian Application No. 2003284005.
Examiner's Interview Record dated Aug. 21, 2009, issued in U.S. Appl. No. 11/752,213, filed May 22, 2007.
Examiner's Interview Record dated May 21, 2008, issued in U.S. Appl. No. 10/628,141, filed Jul. 24, 2003.
Examiner's Interview Record dated Jan. 10, 2008, issued in U.S. Appl. No. 11/752,213, filed May 22, 2007.
Final Office Action dated Apr. 17, 2009, issued in U.S. Appl. No. 11/752,213, filed May 22, 2007.
Final Office Action dated Feb. 25, 2008, issued in U.S. Appl. No. 10/678,767, filed Oct. 3, 2003.
Final Office Action dated Jun. 4, 2009, issued in U.S. Appl. No. 11/835,590, filed Aug. 8, 2007.
Final Office Action dated Mar. 4, 2009, issued in U.S. Appl. No. 10/678,767, filed Oct. 3, 2003.
Final Office Action dated Jul. 2, 2009, issued in U.S. Appl. No. 11/835,620, filed Aug. 8, 2007.
Final Office Action dated Nov. 29, 2006, issued in U.S. Appl. No. 10/623,431, filed Jul. 18, 2003.
Final Office Action dated Oct. 28, 2009, issued in U.S. Appl. No. 10/623,431, filed Jul. 18, 2003.
Final Office Action dated Sep. 13, 2007, issued in U.S. Appl. No. 10/628,141, filed Jul. 24, 2003.
Final Office Action dated Sep. 5, 2008, issued in U.S. Appl. No. 10/623,431, filed Jul. 18, 2003.
First Examination Report for Indian Application No. 496/DELNP/2005, dated Jun. 15, 2006.
International Preliminary Examination Report dated Nov. 14, 2003, issued in International Application No. WO03/053426.
International Preliminary Examination Report dated May 3, 2005, issued in International Application No. WO04/009069.
International Preliminary Report on Patentability/Written Opinion dated Feb. 10, 2009, issued in International Application No. WO08/019388.
International Preliminary Report on Patentability/Written Opinion dated Feb. 10, 2009, issued in International Application No. WO08/021932.
International Search Report dated May 2, 2003, issued in International Application No. WO03/053426.
International Search Report dated Dec. 11, 2003, issued in International Application No. WO04/009069.
International Search Report dated Jun. 3, 2004, issued in International Application No. WO04/030633.
International Search Report dated Sep. 12, 2008, issued in International Application No. WO08/019388.
International Search Report dated Sep. 19, 2008, issued in International Application No. WO08/021932.
International Search Report dated Aug. 21, 2008, issued in International Application No. WO08/147843.

Non-Final Office Action dated Apr. 17, 2006, issued in U.S. Appl. No. 10/623,431, filed Jul. 18, 2003.
Non-Final Office Action dated Apr. 3, 2007, issued in U.S. Appl. No. 10/628,141, filed Jul. 24, 2003.
Non-Final Office Action dated Aug. 12, 2008, issued in U.S. Appl. No. 11/752,213, filed May 22, 2007.
Non-Final Office Action dated Jun. 25, 2009, issued in U.S. Appl. No. 11/752,213, filed May 22, 2007.
Non-Final Office Action dated Aug. 19, 2005, issued in U.S. Appl. No. 10/623,431, filed Jul. 18, 2003.
Non-Final Office Action dated Aug. 22, 2008, issued in U.S. Appl. No. 10/678,767, filed Oct. 3, 2003.
Non-Final Office Action dated Aug. 27, 2007, issued in U.S. Appl. No. 10/678,767, filed Oct. 3, 2003.
Non-Final Office Action dated Dec. 6, 2005, issued in U.S. Appl. No. 10/628,141, filed Jul. 24, 2003.
Non-Final Office Action dated Feb. 20, 2007, issued in U.S. Appl. No. 10/678,767, filed Oct. 3, 2003.
Non-Final Office Action dated Jun. 1, 2006, issued in U.S. Appl. No. 10/628,141, filed Jul. 24, 2003.
Non-Final Office Action dated Mar. 18, 2005, issued, in U.S. Appl. No. 10/623,431, filed Jul. 18, 2003.
Non-Final Office Action dated Oct. 4, 2006, issued, in U.S. Appl. No. 10/628,141, filed Jul. 24, 2003.
Non-Final Office Action dated Oct. 7, 2008 issued, in U.S. Appl. No. 11/835,620, filed Aug. 8, 2007.
Non-Final Office Action dated Sep. 18, 2008, issued in U.S. Appl. No. 11/835,590, filed Aug. 8, 2007.
Non-Final Office Action dated Sep. 27, 2007 issued in U.S. Appl. No. 11/752,213, filed May 22, 2007.
Non-Final Office Action dated Sep. 28, 2007 issued in U.S. Appl. No. 10/623,431, filed Jul. 18, 2003.
Non-Final Office Action dated Sep. 29, 2004, issued in U.S. Appl. No. 10/623,431, filed Jul. 18, 2003.
Non-Final Office Action dated Mar. 17, 2009, issued in U.S. Appl. No. 10/623,431, filed Jul. 18, 2003.
Non-Final Office Action dated Sep. 22, 2008, issued in U.S. Appl. No. 12/035,820, filed Feb. 22, 2008.
PCT International Preliminary Examination Report dated Feb. 5, 2004, issued in International Application No. PCT/US02/35396.
Response to Office Action dated Jan. 23, 2009, in U.S. Appl. No. 10/623,431, filed Jul. 18, 2003.
Response to Office Action dated Apr. 15, 2008, in U.S. Appl. No. 10/678,767, filed Oct. 3, 2003.
Response to Office Action dated Jan. 17, 2007, in U.S. Appl. No. 10/623,431, filed Jul. 18, 2003.
Response to Office dated Nov. 5, 2008, in U.S. Appl. No. 10/623,431, filed Jul. 18, 2003.
Response to Office Action and Applicant Statement of Interview Summary dated Jun. 17, 2009, in U.S. Appl. No. 10/623,431, filed Jul. 18, 2003.
Response to Office Action dated Dec. 12, 2008, in U.S. Appl. No. 11/752,213, filed May 22, 2007.
Response to Office Action dated Dec. 14, 2007, in U.S. Appl. No. 10/623,431, filed Jul. 18, 2003.
Response to Office Action dated Dec. 27, 2007, in U.S. Appl. No. 11/752,213, filed May 22, 2007.
Response to Office Action dated Dec. 29, 2004, in U.S. Appl. No. 10/623,431, filed Jul. 18, 2003.
Response to Office Action dated Jul. 14, 2006, in U.S. Appl. No. 10/623,431, filed Jul. 18, 2003 (CYP 12-00).
Response to Office Action dated Jun. 10, 2005, in U.S. Appl. No. 10/623,431, filed Jul. 18, 2003.
Response to Office Action dated Nov. 16, 2005, in U.S. Appl. No. 10/623,431, filed Jul. 18, 2003.
Response to Office Action dated Jun. 7, 2007, in U.S. Appl. No. 10/678,767, filed Oct. 3, 2003.
Response to Office Action dated Nov. 24, 2008, in U.S. Appl. No. 10/678,767, filed Oct. 3, 2003.
Response to Office Action dated Nov. 27, 2007, in U.S. Appl. No. 10/678,767, filed Oct. 3, 2003.
Response to Restriction Requirement dated Jun. 4, 2008, in U.S. Appl. No. 10/623,431, filed Jul. 18, 2003.

Response to Restriction Requirement dated Mar. 4, 2008, in U.S. Appl. No. 11/752,213, filed May 22, 2007.
Response to Restriction Requirement dated Nov. 16, 2006, in U.S. Appl. No. 10/678,767, filed Oct. 3, 2003.
Response to Restriction Requirement dated Sep. 12, 2005, in U.S. Appl. No. 10/628,141, filed Jul. 24, 2003.
Response dated Jun. 17, 2008, in European Application No. 02793880.2.
Response dated Nov. 24, 2005, in European Application No. 02793880.2.
Restriction Requirement dated Aug. 12, 2005, issued in U.S. Appl. No. 10/628,141, filed Jul. 24, 2003.
Restriction Requirement dated Feb. 4, 2008, issued in U.S. Appl. No. 11/752,213, filed May 22, 2007, Kranzler et al.
Restriction Requirement dated Feb. 4, 2009, issued in U.S. Appl. No. 12/035,820, filed Feb. 22, 2008.
Restriction Requirement dated May 16, 2008, issued in U.S. Appl. No. 10/623,431, filed Jul. 18, 2003.
Restriction Requirement dated Oct. 20, 2006, issued in U.S. Appl. No. 10/678,767, filed Oct. 3, 2003.
Okuda et al., "One case of Sub lumbar Melagra that Responds to Serotonin-Noradrenaline Reuptake Inhibitors and Milnacipran Hydrochloride," *Pain Clinic*, 23:1111-1112 (2002).
Drug Legend, "Toledomin Tablets 15, Toledomin Tablets 25", $5^{th}$ Edition, Jan. 2002.
Higuchi et al., "Handling Milnacipran, Chapter 1, Pharmacokinetic Features, Appropriate Dosage Amount, and Administration Period of Milnacipran," *Japanese Journal of Clinical Psychopharmacology*, 5:903-909 (2002).
Murasaki et al., "Clinical Effect of Milnacipran Hydrochloride (TN-912) in Depression and Depressive States, a New Antidepressant—Dose Finding Study," *Journal of Clinical Therapeutics & Medicine*, 11:85-101 (1995).
Murasaki et al., "Clinical Evaluation of Milnacipran Hydrochloride (TN-912) in Depression and Depressive States, a New Antidepressant," *Journal of Clinical Therapeutics & Medicine*, 11:71-83 (1995).
Wakamatsu, "Preclinical Review of Milnacipran—Part II: Clinical Review-," *Jpn Pharmacology & Therapeutics*, 30:141-155 (2002).
BIOSIS Accession No. PREV200300358583 [onlline], Trzaska et al., "Effects of milnacipran and citalopram on cognitive performance in BALB/c, C57BL/6 and 129S6/SvEv mice", FASEB J., 17(4-5):Abstract 389.1; FASEB Meeting on Experimental Biology: Translating the Genome; San Diego, CA, USA; Apr. 11-15, 2003.
European Application No. 06804211.8: Supplementary European Search Report, dated Jul. 23, 2010.
European Application No. 03776232.5: Communication pursuant to Article 94(3) EPC, dated Jan. 10, 2011.
European Application No. 03776232.5: Supplementary European Search Report, dated Aug. 9, 2010.
European Application No. 07800061.9: Supplementary European Search Report, dated Aug. 11, 2010.
European Application No. 07840805.1: Supplementary European Search Report, dated Jul. 23, 2010.
European Application No. 08769586.2: Supplementary European Search Report, dated Jul. 7, 2010.
Gendreau et al. "Efficacy of Milnacipran in Patients with Fibromyalgia" J. Rheumatol., 32(10):1975-1984 (2005).
International Preliminary Report on Patentability and Written Opinion for PCT/US2006/037714, dated Apr. 1, 2008.
International Search Report for PCT/US02/35396, dated Feb. 28, 2003.
International Search Report for PCT/US2006/037714, dated Aug. 23, 2007.
Medline Accession No. NLM12363125 [onlline], Hirschfeld et al. "Partial response and nonresponse to antidepressant therapy: current approaches and treatment options", J. Clin. Psychiatry, 63(9):826-837 (2002) (abstract).
Medline Accession No. NLM12766929 [onlline], Higuchi et al. "Milnacipran plasma levels and antidepressant response in Japanese major depressive patients", Human Psychopharmacology, 18(4):255-259 (2003) (abstract).

Medline Accession No. NLM1821700 [onlline], Annsseau et al., "Interest of a loading dose of milnacipran in endogenous depressive inpatients. Comparison with the standard regimen and with fluvoxamine", (1991) (abstract).
Medline Accession No. NLM2569214 [onlline], Annsseau et al., "Controlled comparison of two doses of milnacipran (F 2207) and amitriptyline in major depressive inpatients", Psychopharmacology, 98(2):163-168 (1989) (abstract).
Nagaoka et al., "One Case of Fibromyalgia Syndrome That Responds Completely With Serotonin/Noradrenaline Reuptake Inhibitor (SNRI)", Medicine & Drug Journal, 37:3036-3038 (2001) (Japanese).
Novick et al. 2002. A randomized, double-blind, placebo-controlled trial of tegaserod in female patients suffering from irritable bowel syndrome with constipation. Aliment Pharmacol Ther 16:1877-88.
Tajima, "Japanese experience with dual-action antidepressants", International Clinical Psychopharmacology, 17(Suppl. 1):S37-S42 (2002).
U.S. Appl. No. 10/623,431, filed Jul. 18, 2003 by Kranzler et al.: Response and Amendment Accompanying RCE, dated Apr. 15, 2010.
U.S. Appl. No. 10/623,431, filed Jul. 18, 2003 by Kranzler et al.: Notice of Allowance, dated Jun. 17, 2010.
U.S. Appl. No. 10/678,767, filed Oct. 3, 2003 by Rao et al.: Non-Final Office Action, dated Jan. 8, 2010.
U.S. Appl. No. 12/035,820, filed Feb. 22, 2008 by Kranzler et al.: Response to Notice of Non-Compliant Amendment (37 C.F.R. § 1.121), dated Aug. 27, 2009.
U.S. Appl. No. 12/035,820, filed Feb. 22, 2008 by Kranzler et al.: Final Office Action, dated Nov. 27, 2009.
U.S. Appl. No. 12/035,820, filed Feb. 22, 2008 by Kranzler et al.: Examiner's Interview Summary Record, dated Mar. 15, 2010.
U.S. Appl. No. 12/035,820, filed Feb. 22, 2008 by Kranzler et al.: Amendment Accompanying Request for Continued Examination, dated Apr. 15, 2010.
U.S. Appl. No. 12/035,820, filed Feb. 22, 2008 by Kranzler et al.: Notice of Allowance, dated Dec. 17, 2010.
U.S. Appl. No. 12/125,302, filed May 22, 2008 by Rao et al.: Non-Final Office Action, dated Nov. 23, 2009.
U.S. Appl. No. 12/630,693, filed Dec. 3, 2009 by Rao et al.: Non-Final Office Action, dated May 17, 2010.
U.S. Appl. No. 12/644,510, filed Dec. 22, 2009 by Kranzler et al.: Preliminary Amendment, dated Apr. 15, 2010.
U.S. Appl. No. 12/644,510, filed Dec. 22, 2009 by Kranzler et al.: Notice of Allowance, dated Nov. 30, 2010.
U.S. Appl. No. 12/647,915, filed Dec. 28, 2009 by Kranzler et al.: Preliminary Amendment, dated Dec. 28, 2009.
Vercoulen et al., The Lancet, 347:858-861 (1996).
Woolf, C. et al., "Neuropathic pain: aetiology, symptoms, mechanisms, and management", Lancet, vol. 353, No. 9168, (1999), pp. 1959-1964.
Zeltser et al., "Comparison of autotomy behavior induced in rats by various clinically-used neurectomy methods", Pain, 89:19-24 (2000).
Aaron et al., "A review of the evidence for overlap among unexplained clinical conditions", Ann. Intern. Med., vol. 134, No. 9.2, (2001), pp. 868-881.
Aaron et al., "Overlapping conditions among patients with chronic fatigue syndrome, fibromyalgia, and temporomandibular disorder", Arch. Intern. Med., vol. 160, No. 2, (2000), pp. 221-227.
Alagiri et al. "Interstitial Cystitis: Unexplained Associations with other Chronic Disease and Pain Syndromes," Urology 49 (Suppl. 5A): 52-57, 1997.
Ansari, A., "The Efficacy of Newer Antidepressants in the Treatment of Chronic Pain: A Review of Current Literature", Harv. Rev. Psych., vol. 7, No. 5, (2000), pp. 257-277.
Ardid et al., "Antidepressants and pain", La Lettre De Parmacologue, vol. 13, No. 8, (Oct. 1993), pp. 191-195.
Atkinson et al., "Effects of noradrenergic and sertonergic antidepressants on chronic low back pain intensity", Pain, vol. 83, No. 2, (1999), pp. 137-145.
Barkin, R., "The Management Challenges of Chronic Pain: The Roll of Antidepressants", American Journal of Therapeutics, vol. 7, (Jan. 2000), pp. 31-47.

Bel et al., "Modulation of the extracellular 5-hydroxytryptamine brain concentrations by the serotonin and noradrenaline reuptake inhibitor, milnacipran. Microdialysis studies in rats", Neuropsychopharmacology, vol. 21, No. 6, (1999), pp. 745-754.
Bennett et al., 1988, Pain, 33:87-107.
Boissevain et al., "Toward an integrated understanding of fibromyalgia syndrome. I. Medical and pathophysiological aspects", Pain, vol. 45, No. 3, (1991), pp. 227-38.
Briley, "New hope in the treatment of painful symptoms in depression," Curr. Opin. Invest. Drugs (2003) 4(1): 42-45. Abstract.
Briley, M., "Milnacipran, A Double Noradrenaline and Serotonin Reuptake Inhibiting Antidepressant", European Neuropsychopharmacology, vol. 6, Suppl. 4, p. S4 (Sep. 1996).
Buskila, D., "Drug Therapy", Baillieres Best Practice Research Clinical Rheumatol., vol. 13, No. 3, (1999), pp. 479-485.
Bymaster et al., "Comparative Affinity of Duloxetine and Venlafaxine for Serotonin and Norepinephrine Transporters in vitro and in vivo", Human Serotonin Receptor Subtypes, and Other Neuronal Receptors, Neuropsychopharmacology, vol. 25 (2001) pp. 871-880.
Caccia, "Metabolism of the newer antidepressants: an overview of the pharmacological and pharmacokinetic implications", Clin. Pharmacokinet., vol. 34, No. 4, (1998), pp. 281-302.
Chart of Cypress Bioscience applications related to milnacipran for treatment of various disorders, 2009.
Clauw, "The pathogenesis of chronic pain and fatigue syndromes, with special reference to fibromyalgia", Med. Hypotheses, vol. 44, No. 5, (1995), pp. 369-378.
Cypress Bioscience, Inc., Investor Fact Sheet, Aug. 2001.
Decosterd et al., 2000, Pain 87:149-158.
Deprez et al., "Which bioequivalence study for a racemic drug Application to milnacipran?", Eur. J. Drug Metab. Pharmacokinet., vol. 23, No. 2, (1998), pp. 166-171.
Doyle & Hu, "A new enantioselective synthesis of milnacipran and an analogue by catalytic asymmetric cyclopropanation", Adv. Synth. Catal., vol. 343, No. 3, (2001), pp. 299-302.
Drugu AN 1983-01770, Woerz zum Thema R, Muench. Med. Wochenschr. 124(40) 855-56, 1982, abstract.
Drugu AN 1992-39596, Monreau, G. et al., Fundam. Clin. Pharmacol., 6(4-5) 226, 1992, abstract.
Dryson, E., "Venlafaxine and fibromyalgia", NZ Med. J., vol. 87, 113(1105), Mar. 10, 2000.
Dworkin et al., "Clinical Aspects of Depression in Chronic Pain Patients," Clin. J. Pain, vol. 7, No. 2, (Jun. 1991), pp. 79-94.
Eisen, "Venflaxine therapy for vulvodynia", The Pain Clinic, vol. 8, No. 4, (1995), pp. 365-367.
Embase AN 1998 129084, Prescrire Enternational, 1998, 7/34, 51-53, abstract.
Embase AN 90228858, Macher J. et al. Neuropsychobiology, 1989, 22/2, 77-82, abstract.
Farthing, "Irritable Bowel Syndrome: New Pharmaceutical Approaches to Treatment", Baillliere's Clinical Gastroenterology, vol. 13 No. 3, (1999), pp. 461-471.
Fishbain, D., "Evidence-based data on pain relief with antidepressants", Ann. Med., (2000), vol. 32, pp. 305-316.
Giamberardino, "Recent and forgotten aspects of visceral pain", Eur. J. Pain, vol. 3, (1999), pp. 77-92.
Goldenberg et al., "A Randomized, Controlled Trial of Amitriptyline and Naproxen in the Treatment of Patients with Fibromyalgia", Arthritis Rheumatism, vol. 29, No. 11, (1986), pp. 1371-1377.
Goodnick et al., "Psychotropic treatment of chronic fatigue syndrome and related disorders", J. Clin. Psychiatry, (1993), pp. 13-20.
Gruber et al., "The management of treatment-resistant depression in disorders on the interface of psychiatry and medicine. Fibromyalgia, chronic fatigue syndrome, migraine, irritable bowel syndrome, atypical facial pain, and premenstrul dysphoric disorder," The Psychiatric Clinics of North America 19:351369 (1995).
Hannonen et al., "A Randomized, double-blind, placebo-controlled study of miclobemide and amitriptyline in the treatment of fibromyalgia in females without psychiatric disorder", British Journal of Rheumatology, vol. 37, No. 12, (1998), pp. 1279-1286.

Hara et al., "The Effects of Tramadol and its Metabolite on Glycine, Aminobutyric Acid A, and N-Methyl-D-Aspartate Receptors Expressed in Xenopus Oocytes." Anesth. Analg., 100:1400-1405 (2005).
Jain, "Addressing both the emotional and physical symptoms in depression," Medscape CME program (2003).
Jasmin et al., 1998, Pain 75:367-382.
Jung et al., "The Efficacy of Selective Seratonin Reuptake Inhibitors for the Management of Chronic Pain", J. Gen. Intern. Med., vol. 12, No. 6, (1997), pp. 384-389.
Kasper et al., "A placebo-controlled study of pregabalin and venlafaxine treatment of GAD", European neuropsychopharmacology, vol. 12, Suppl. 3, (Oct. 2002), pp. S341-S342.
Kent, J., "SNaris, NaSSAs, and NaRIs: new agents for the treatment of depression", Lancet, vol. 355, No. 9207, (2000), pp. 911-918.
Kim et al., 1992, Pain 50:355-363.
Kranzler, J. et al., "The Psychopharmacology of Fibromyalgia: A Drug Development Perspective", vol. 36, No. 1, (2002), pp. 165-213.
Martindale, Antidepressants, (1999), Pharmaceutical Press, London, 32 XP002387013.
Max et al., "Effects of Desipramine, Amitriptyline, and Fluoxetine on pain diabetic neuropathy", New England Journal of Medicine, vol. 326, No. 19, (1992), pp. 1250-1256.
Medline AN 2001240387, Enggaard et al., Clin. Pharmacol. Therapeutics, 2001, Apr. 69(4), 245-54, abstract.
Medline AN 2001337451, Barkin et al., Am. J. Therapeutics, Jan. 2000, 7(1) 31-47, abstract.
Medline AN 97229930, Lewis et al., Am. J. health-system pharmacy, Mar. 15, 1997, 54(6), 643-52, abstract.
Medline AN 97363915, Aronson, Clin. Therapeutics, May-Jun. 1997, 19(3) 420-32, abstract.
Montgomery, "Venlafaxine: a new dimension in antidepressant pharmacotherapy", J. Clin. Psychiatry, vol. 54, No. 3, (Mar. 1993), pp. 119-126.
Moret et al., "Biochemical profile of midalcipran (F 2207), 1-phenyl-1-diethyl-aminocarbonyl-2-aminomethyl-cyclopropane (Z) hydrochloride, a potential fourth generation antidepressant drug", Neuropharmacology, vol. 24, No. 12, (1985), pp. 1211-1219.
Moret et al., "Effects of milnacipran and pindolol on extracellular noradrenaline and serotonin levels in guinea pig hypothalamus", J. Neurochem., vol. 69, No. 2, (1997), pp. 815-822.
Moret et al., "Sensitivity of the response of 5-HT autoreceptors to drugs modifying synaptic availability of 5-HT", Neuropharmacology, vol. 27, No. 1, (1988), pp. 43-49.
Nagaoka et al., "Beneficial Effects of a Serotonin-Noradrenaline Reuptake Inhibitor on Fibromyalgia Syndrome: A Case Report", Medicine and Drug Journal, vol. 37, No. 10, (Oct. 1, 2001), pp. 238-240.
Nicolodi et al. 1998. Fibromyalgia and headache. Failure of serotonergic analgesia and N-methyl-d-aspartate-mediated neuronal plasticity: their common clues. Cephalgia Supp.21 pp. 41-44.
Ninan, P., "Use of Venlafacine in Other Psychiatric Disorders", Depression and Anxiety, vol. 12, No. 1, (2000), pp. 90-94.
Noguchi et al., "Open Channel Block of NMDA Receptors by Conformationally Receptors Restricted Analogs of Milnacipran and Their Protective Effect Against NMDA-Induced Neurotoxicity", Synapse, vol. 31, (1999), pp. 87-96.
Nutt et al., "Potential applications of veniafaxine", Rev. Contemp. Pharmacother., vol. 9, (1998), pp. 321-331.
Palmier et al., "Monoamine uptake inhibition by plasma from healthy volunteers after single oral doses of the antidepressant milnacipran", Eur. J. Clin. Pharmacol., vol. 37, No. 3, (1989), pp. 235-238.
Pande, A.C. et al., "Three randomised, placebo-controlled, double-blind trials of pregabalin treatment of Generalized Anxiety Disorder (GAD)", vol. 10, Suppl. 3, (2000), pp. 344.
Peghini et al. 1998. Imipramine decreases oesophageal pain perception in human male volunteers. Gut 42:807-13.
Puech et al., "Milnacipran, a new serotonin and noradrenaline reuptake inhibitor: an overview of its antidepressant activity and clinical tolerability", Int. J. Psychopharm., vol. 12, (1997), pp. 99-108.

Quijada-Carrera et al., "Comparison of tenoxicam and bromazepan in the treatment of fibromyalgia: a randomized, double-blind, placebo-controlled trial", Pain, vol. 65, No. 2-3, (1996), pp. 221-225.

Quintero et al., 2000, Pharmacology, Biochemistry and Behavior 67:449-458.

Rao et al., "The neuropharmacology of centrally-acting analgesic medications in fibromyalgia", Rheum. Dis. Clin. N. Amer., vol. 28, (2002), pp. 235-259.

Rao, S. et al., "Pharmacological therapies in fibromyalgia", Best Practice & Research Clinical Rheumatology, vol. 17, No. 4, (2003), pp. 611-627.

Reid et al., 2000, British Medical Journal 320:292-296.

Driessen, Reimann et al., "Effects of the Central Analgesic Tramadol on the Uptake and Release of Noradrenalineand dopamine in vitro", Br. J. Pharmacol, vol. 108, No. 3, (Mar. 1993), pp. 806-811.

Driessen, Reimann et al., "Interaction of the Central Analgesic Tramadol with the Uptake and Release of 5-hydroxytryptamine in the rat brain in vitro", Br. J. Pharmacol, vol. 105, No. 1, (Jan. 1992), pp. 147-151.

Reneric et al., "Antidepressant Behavioural Effects by Dual Inhibition of Monoamine Reuptake in the Rat Forced Swimming Test", Psychopharmacology, vol. 136 (1998), pp. 190-197.

Ruoff, G., "Depression in the Patient with Chronic Pain", The Journal of Family Practice, vol. 43, No. 6, (1996), pp. S25-S33.

Sanchez, C. and Hytell, J., "Comparison of the Effects of Antidepressants and Their Metabolites on Reuptake of Biogenic Amines and on Receptor Binding", Cellular Molecular Neurobiology, vol. 19, No. 4, (1999), pp. 467-489.

Saper et al., "Nefazodone for Chronic Daily Headache Prophylaxis: An Open-Label Study", Headache, vol. 41, No. 5, (2001), pp. 465-474.

Seltzer et al., 1990, Pain 43:205-218.

Shuto et al., "(+)-(Z)-2-(Aminomethyl)-1-phenycyclopropanecarboximide Derivatives as a New Prototype of NMDA Receptor Antagonists", J. Med. Chem., vol. 38, (1995), pp. 2964-2968.

Shuto et al., "(1s,2R)-1-Phenyl-2-[(S)-1-aminopropyl]-N, N-diethylcyclopropanecarboxamide (PPDC), a New Class of NMDA-Receptor Antagonist: Molecular Design by a Novel Conformational Restriction Strategy", Jpn. J. Pharmacol., vol. 85, (2001), pp. 207-213.

Shuto et al., "Synthesis and Biological Activity of Conformationally Restricted Analogs of Milnacipran: (1s,2R)-1-Phenyl-2-[(S)-1-aminopropyl]-N, N-diethylcyclopropanecarboxamide, an Efficient Noncompetitive N-Methyl-D-aspartic Acid Receptor Antagonist", J. Med. Chem., 39:4844-4851 (1996).

Shuto et al., "Synthesis and Biological Activity of Conformationally Restricted Analogs of Milnacipran: (1s,2R)-1-Phenyl-2-[(S)-1-aminopropyl]-N, N-diethylcyclopropanecarboxamide, Is a Novel Class of NMDA Receptor Channel Blocker", J. Med. Chem., 41:3507-3514 (1998).

Shuto et al., "Synthesis of (+) and (−) milnaciprans and their conformationally restricted analogs", Tetrahedron Lett., vol. 37, No. 5, (1996), pp. 641-644.

Spencer et al., "Milnacipran—A review of its use in depression", Drugs, vol. 56, No. 3, (1998), pp. 405-427.

Sawynok et al., "Peripheral Antinociceptive Actions of Desipramine and Fluoxetine in an Inflammatory and Neuropathic Pain Test in the Rat", Pain vol. 82, (1999), pp. 149-158.

Tatsumi et al., 1997, European Journal of Pharmacology 340:249-258.

Thema. 1982. The drug induced alleviation of carcinoma pain. Much Med Wochenschr 124:855-56.

Turcotte et al., "Assessment of the serotonin and norepinephrine reuptake blocking properties of duloxetine in healthy subjects", Neuropsychopharmacology, vol. 24, No. 5, (2001), pp. 511-521.

Vaishnavi. 2004. Milnacipran: A comparative analysis of human monoamine uptake and transporter binding affinity. Biol Psychiatry 55:320-22.

Viazzo et al., "Microbiological transformations 34: enantioselective hydrolysis of a keyactone involved in the synthesis of the antidepressant milnacipran", Tetrahedron Lett., vol. 37, No. 26, (1996), pp. 4519-4522.

Vitton et al. 2004. A double-blind placebo-controlled trial of milnacipran in the treatment of fibromyalgia. Hum Psychopharmacol Clin Exp 19:S27-35.

Watson et al., "Amitriptyline versus maprotiline in postherpetic neuralgia: a randomized, double-blind, crossover trial", Pain, vol. 48, No. 1, (1992), pp. 29-36.

Wesselman et al. 2001. Interstitial cystitis: A chronic visceral pain syndrome. Urology 57(supp. 6A):32-39.

Wessely et al. 1999. Functional somatic syndromes: one or many? Lancet 354:936-39.

Witter et al. 2003. Chronic pain and fibromyalgia: the regulatory perspective. Best Practice Res Clin Rheumatology 17(4):541-46.

Woolf, C. et al., "Evidence for a Central Component of Post-Injury Pain Hypersensitivity", Nature, vol. 306, No. 5944, (1983), pp. 686-688.

Yoshimura et al., "The involvement of the tetrodotoxin-resistant sodium channel Nav1.8 (PN3/SNS) in a rat model of visceral pain", J. Neurosci., vol. 21, No. 21, (2001), pp. 8690-8696.

Yunus et al., "Towards a Model of Pathophysiology of Fibromyalgia: Aberrant Central Pain Mechanisms with Peripheral Modulation," J. Rheumatol., vol. 19, No. 6, (1992), pp. 846-850.

Yunus et al., "Short term effects of ibuprofen in primary fibromyalgia syndrome" J. Rheumatol., vol. 16, No. 4, (1989), pp. 527-532.

MILNACIPRAN FOR THE LONG-TERM TREATMENT OF FIBROMYALGIA SYNDROME

CROSS-REFERENCE TO RELATED APPLICATION

The present application claims priority to U.S. provisional patent application Ser. No. 60/721,722, filed Sep. 28, 2005, which is hereby incorporated by reference in its entirety.

FIELD OF THE INVENTION

The present invention relates to the long-term treatment of fibromyalgia and its symptoms by administering to a patient suffering from fibromyalgia a dual norepinephrine serotonin reuptake inhibitor. More particularly, the present invention relates to the long-term treatment of fibromyalgia and its symptoms by administering to a patient suffering from fibromyalgia a dual norepinephrine serotonin reuptake inhibitor that inhibits the reuptake of norepinephrine to an equal or greater extent than it inhibits the reuptake of serotonin.

BACKGROUND

Fibromyalgia, also known as the fibromyalgia syndrome (FMS) is a common systemic rheumatologic disorder estimated to affect 2% to 4% of the population, second in prevalence among rheumatologic conditions only to osteoarthritis. Wolfe et al., Arthritis Rheum. 1990; 33(2):160-172; Wolfe et al., Arthritis Rheum. 1995; 38(1):19-28. Fibromyalgia is associated with a reduced threshold for pain, generally identified by an increased sensitivity to pressure all over the body, and is often accompanied by fatigue, sleep disturbance, and morning stiffness. Other common symptoms include headache, migraine, variable bowel habits, diffuse abdominal pain, and urinary frequency. The diagnostic criteria for fibromyalgia require not only a history of widespread pain, but also the finding of tenderness on physical examination ("tender points"). In order to fulfill the criteria for fibromyalgia established in 1990 by the American College of Rheumatology (ACR), an individual must have both widespread pain involving all four quadrants of the body as well as the axial skeleton and the presence of 11 of 18 tender points on examination. Wolfe et al., Arthritis Rheum. 1990; 33(2):160-172.

While there has been some suggestion that FMS may represent a form of somatization disorder, there is increasing evidence and acceptance that FMS is a medical problem, reflecting a generalized heightened perception of sensory stimuli. The abnormality is thought to occur within the central nervous system (CNS) rather than peripherally, and the proposed pathophysiological defect is termed "central sensitization." Clauw D J and Chrousos G P, Neuroimmunomodulation 1997; 4(3):134-153; Yunas M B, J Rheumatol. 1992; 19(6):846-850; Bradley et al., Curr Rheumatol Rep. 2000; 2(2):141-148; Simms R W, Am J Med Sci. 1998; 315(6):346-350. FMS patients typically suffer from both allodynia (perceiving pain even from a non-painful stimulus such as light touch) and hyperalgesia (an augmentation of pain processing in which a painful stimulus is magnified and perceived with higher intensity than it would be by a normal volunteer). Mountz et al., Arthritis & Rheumatism 1995; 38(7):926-938; Arroyo J F and Cohen M L, J Rheumatol. 1993; 20(11):1925-1931. In this regard, there are many parallels in its clinical presentation and proposed underlying mechanisms with neuropathic pain, such as diabetic neuropathy and trigeminal neuralgia. Sindrup S H and T S Jensen, Pain 1999; 83(3):389-400; Woolf C J, Nature 1983; 306(5944):686-688; Woolf C J and R J Mannion, Lancet 1999; 353(9168):1959-1964. As a result, FMS is treated today primarily within this medical model. It is most often diagnosed in the primary care setting, and almost half of the office visits are to internal medicine and family practice providers (1998 National Ambulatory Medical Care Survey). Visits to rheumatologists account for 16% of FMS patients' office visits. The remainder of visits are to a variety of tertiary care providers, including pain centers, physical medicine specialists, and psychiatrists.

Individuals with fibromyalgia suffer from a number of other symptoms, including a high incidence of recurrent non-cardiac chest pain, heartburn, palpitations, and irritable bowel syndrome. Wolfe, et al., Arthritis Rheum. 1990; 33(2):160-172; Mukerji et al., Angiology 1995; 46(5):425-430. Although the physiologic basis of these symptoms remains unclear, increasing evidence suggests that dysfunction of the autonomic nervous system is common in fibromyalgia and related illnesses. Clauw D J and Chrousos G P, Neuroimmunomodulation 1997; 4(3):134-153; Freeman R and Komaroff A L, Am J Med. 1997; 102(4):357-364. Prospective studies of randomly selected individuals with fibromyalgia have detected objective evidence of dysfunction of several visceral organs, including a 75% incidence of echocardiographic evidence of mitral valve prolapse, a 40-70% incidence of esophageal dysmotility, and diminished static inspiratory and expiratory pressures on pulmonary function testing. Lurie et al., Scand J Rehab Med. 1990; 22(3):151-155; Pellegrino et al., Arch Phys Med Rehab. 1989; 70(7):541-543. Neurally-mediated hypotension and syncope also appear to occur more frequently in individuals with fibromyalgia. Rowe et al., Lancet 1995; 345(8950):623-624. Fibromyalgia is also associated with high rates of disability, increased health care utilization, more frequent psychiatric consultations and a greater number of lifetime psychiatric diagnoses than controls.

Fibromyalgia research has recently emerged as a significant area of investigation separate from the study of other chronic pain conditions. A significant body of literature already supports the use of tricyclic antidepressants for FMS, and there are a few other controlled studies evaluating the efficacy of other therapeutic agents as well. However, the interpretation of trial data is complicated by factors such as the lack of an accepted binary definition of a "responder" versus a "non-responder," as is now commonly used for trials of other rheumatological conditions, such as Rheumatoid Arthritis. Felson et al., Arthritis Rheum. 1993; 36(6):729-740; Felson D T, J Rheumatol. 1993; 20(3):581-534. In addition, there is no consensus regarding many aspects of trial design, including the designation of appropriate end-points. Nonetheless, there is general agreement that the measurement and characterization of patients' pain is of paramount importance in the determination of an agent's effectiveness in FMS; assessments of fatigue, sleep, depression, physical functionality and overall well-being help to further illuminate an agent's overall effectiveness.

A broad array of medication has been used 'off-label' in patients with FMS with varying degrees of success. Buskila D, Baillieres Best Pract Res Clin Rheumatol. 1999; 13(3):479-485; Leventhal L J, Ann Intern Med. 1999; 131(11):850-858; Lautenschlager J, Scand J Rheumatol Suppl. 2000:113:32-36. While antidepressants are the cornerstone of many treatment paradigms, other agents such as anti-convulsants, antispasticity agents, anxiolytics, sedatives, and opiates have been used. Non-steroidal anti-inflammatory drugs (NSAIDs) and acetaminophen are also used by a large number of patients (Wolfe et al., Arthritis Rheum. 1997; 40(9):1571-1579), even though peripheral inflammation has not been demonstrated (Clauw D J and Chrousos G P, Neuroimmunomodulation 1997; 4(3):134-153), and numerous studies have failed to confirm their effectiveness as analgesics in FMS. Goldenberg et al., Arthritis Rheum. 1986; 29(11):1371-1377; Yunus et al., J Rheumatol. 1989; 16(4):527-532; Wolfe et al., Arthritis Rheum. 2000; 43(2):378-385; Russell et al., Arthritis Rheum. 1991; 34(5):552-560; Quijada-Carrera et al., Pain 1996; 65(2-3):221-225. These agents do, however, provide an element of protection against other peripheral pain generators, such as osteoarthritis.

Antidepressants of all varieties represent a common form of therapy for many chronic pain states, including FMS. Sindrup S H and Jensen T S, Pain 1999; 83(3):389-400; Buskila D, Baillieres Best Pract Res Clin Rheumatol. 1999; 13(3):479-485; Leventhal L J, Ann Intern Med. 1999; 131 (11):850-858; Lautenschlager J, Scand J Rheumatol Suppl. 2000; 113:32-36; Bennett R M, J Functional Syndromes 2001; 1(1):79-92. The majority of available antidepressants directly and/or indirectly increase the levels of 5-HT and/or NE in the CNS. Monoaminergic levels are increased either by inhibiting re-uptake (by blocking transport proteins) or interfering with the breakdown of the monoamine (by inhibiting the monoamine oxidase enzymes) after its release into the synaptic cleft.

Tricyclic Antidepressants (TCAs)

The TCAs most commonly employed in the treatment of FMS include amitriptyline, doxepin, and cyclobenzaprine. Buskila D, Baillieres Best Pract Res Clin Rheumatol. 1999; 13(3):479-485; Lautenschlager J, Scand J Rheumatol Suppl. 2000; 113:32-36; Bennett R M, J Functional Syndromes 2001; 1(1):79-92. While cyclobenzaprine is typically classified as a muscle relaxant, rather than an antidepressant, it shares structural and pharmacological similarities with the TCAs, although its sedating qualities often override its usefulness in other applications. Kobayashi et al., Eur J Pharmacol. 1996; 311(1):29-35. TCAs block the re-uptake of both 5-HT and NE, but favor NE re-uptake blockade, and the efficacy of TCAs can be interpreted to support the primacy of NE agonism for analgesic activity. However, TCA's additional anti-cholinergic, antihistaminergic, and α-adrenergic receptor blockade activities impart a wide assortment of undesirable side effects, which often compromise their tolerability and clinical acceptance. Kent J M, Lancet 2000; 355 (9207):911-918.

TCAs have demonstrated moderate efficacy for the treatment of neuropathic pain conditions such as post-herpetic neuralgia and painful diabetic neuropathy. Max et al., Neurology 1988; 38(9):1427-1432; Max et al., N Eng J Med. 1992; 326(19):1250-1256; Watson et al., Neurology 1982; 32(6):671-673; Watson et al., Pain 1992; 48(1):29-36. Multiple studies of TCAs in the treatment of FMS support their use for this syndrome as well, and TCAs have frequently been used as the positive controls to which newer agents have been compared. Max et al., N Eng J Med. 1992; 326(19):1250-1256; Watson et al., Pain 1992; 48(1):29-36; Hannonen et al., Br J Rheumatol. 1998; 37(12):1279-1286; Goldenberg et al., Arthritis & Rheumatism 1996; 39(11):1852-1859.

Selective Serotonin Re-Uptake Inhibitors (SSRIs)

The SSRIs have revolutionized the treatment of depression with their improved side-effect profile secondary to more selective re-uptake inhibition. The SSRI agents fluoxetine, sertraline and citolopram have each been evaluated in randomized, placebo controlled trials in FMS. Goldenberg et al., Arthritis & Rheumatism 1996; 39(11):1852-1859; Wolfe et al., Scand J Rheum. 1994; 23(5):255-259; Anderberg et al., Eur J Pain 2000; 4(1):27-35; Norregaard et al., Pain 1995; 61(3):445-449. However, the results of these trials have been somewhat inconsistent, leaving much debate regarding the relative efficacy of the SSRIs, especially in comparison to TCAs.

Two placebo-controlled trials of citalopram, the most 5-HT-specific of the SSRIs, in FMS patients were both convincingly negative. Anderberg et al., Eur J Pain, 2000; 4(1): 27-35; Norregaard et al., Pain 1995; 61(3):445-449. This suggests that serotonergic enhancement alone is not sufficient to impart analgesia in the chronic pain setting. In fact, based on the evidence assembled to date, the SSRIs, as a class, are generally less efficacious than the TCAs in chronic pain states (Max et al., N Engl J Med. 1992; 326(19):1250-1256; Ansari A, Harv Rev Psych. 2000; 7(5):257-277; Atkinson et al., Pain 1999; 83(2):137-145; Jung et al., J Gen Intern Med. 1997; 12(6):384-389) although there are some exceptions (Saper et al., Headache 2001; 41(5):465-474).

Dual Re-Uptake Inhibitors

Dual re-uptake inhibitors (DRI's) are pharmacologically similar to TCAs (such as amitriptyline and doxepin), exhibiting activity upon both 5-HT and NE re-uptake. Sanchez C and Hytell J, Cell Mol Neurobiol. 1999; 19(4):467-489. Fortunately, these newer agents are generally devoid of significant activity at other receptor systems, resulting in diminished side effects and enhanced tolerability vs. TCA's. Therefore, this class of antidepressant may have significant potential for the treatment of FMS and/or other chronic pain conditions. DRIs that are commercially available in the U.S. include venlafaxine and duloxetine. A number of DRIs are in clinical development; these include milnacipran, bicifadine, viloxazine, LY-113821, SEP-227162, AD-337, and desvenlafaxine succinate (DVS-233).

An open-label trial of venlafaxine (EFFEXOR®) in 15 patients with FMS has been disclosed. Dwight et al., Psychosomatics 1998; 39(1):14-17. Of the 11 patients that completed the study, 6 patients had a positive response to venlafaxine, which was defined as 50% or greater improvement in two different measurements of overall pain. Insomnia was the most common side effect reported, requiring adjunctive medical therapy in 3 of 11 completing patients.

U.S. Pat. No. 6,602,911 describes the use of milnacipran for the treatment of FMS and its symptoms, the entire disclosure of which is incorporated herein by reference.

Opioids

Opiates exert their anti-nocioreceptive effects at various locations within both the ascending and descending pain pathways. Duale et al., Neuroreport 2001; 12(10):2091-2096; Besse et al., Brain Res. 1990; 521(1-2):15-22; Fields et al., Nature 1983; 306(5944):684-686; opioids in chronic pain conditions are widely discussed and debated. Bennett R M, J Functional Syndromes 2001; 1(1):79-92. However, opioids are used by some in the clinical management of FMS, especially when other analgesics have failed to provide sufficient relief. Bennett R M, Mayo Clin Proc. 1999; 74(4):385-398.

The majority of patients with fibromyalgia syndrome remain symptomatic for years. (Carette et al., Arthritis & Rheumatism 1994; 37(1):32-40, 32-33, 39). Carette et al. reported the results of a clinical trial in which amitriptyline (a tricyclic antidepressant), cyclobenzaprine (a muscle relaxant structurally similar to tricyclic antidepressants) and placebo were administered to subjects suffering from fibromyalgia syndrome (Carette et al., Arthritis & Rheumatism 1994; 37(1):32-40). After one month, 21% of the amitryptyline subjects, 12% of the cyclobenzaprine subjects, and 0% of the placebo subjects had significant clinical improvement. At three months, there was no difference between either treatment group and placebo. At six months, no long-term efficacy could be demonstrated because of a higher than expected placebo response, i.e., 19% improvement with placebo.

Thus, there remains a need for an effective, long-term treatment of fibromyalgia syndrome and its symptoms.

SUMMARY OF THE INVENTION

No compound, even if it has benefits for the short-term (acute) treatment of fibromyalgia and its symptoms, has been shown to provide a durable effect such that it provides effective, long-term treatment for fibromyalgia and its symptoms. Surprisingly, according to the methods of the present invention, the administration of a dual norepinephrine serotonin reuptake inhibitor (DRI) to a patient suffering from fibromyalgia syndrome provides effective, long-term treatment of fibromyalgia and its symptoms.

The double-blind, randomized, placebo-controlled clinical study, first reported here in Example 1 below, unexpectedly showed that a DRI may be used to provide effective long-term (e.g., at least three months) treatment for fibromyalgia and its symptoms in patients suffering from fibromyalagia. Further, the results of this clinical study surprisingly showed that a DRI may be used to provide effective, long-term treatment of FMS and its symptoms for at least 6 months.

Thus, the present invention provides methods of long-term treatment of fibromyalgia syndrome in a patient in need thereof comprising administering a DRI to the patient for at least three months. In some embodiments, the DRI is a compound that inhibits norepinephrine reuptake more than or equal to serotonin reuptake (NSRI). In exemplary embodiments, the NSRI is milnacipran.

For example, according to the methods of the present invention, long-term treatment of FMS and its symptoms may be provided to a patient suffering from FMS by administering 25 mg per day to 400 mg per day of milnacipran. In exemplary embodiments, milnacipran may be administered in a dose of 100 mg per day for the long-term treatment of FMS and its symptoms in a patient suffering from FMS. In other exemplary embodiments, milnacipran may be administered in a dose of 200 mg per day for the long-term treatment of FMS and its symptoms in a patient suffering from FMS.

DETAILED DESCRIPTION

Figure 1:
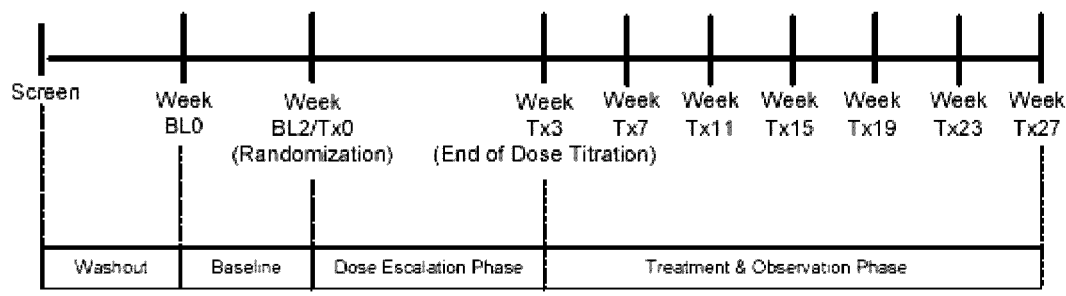
FIG. 1 is a timeline of the clinical study described in Example 1.

As used herein, the term "subject" or "patient" includes human and non-human mammals.

As used herein, "treatment" or "effective treatment" means to relieve, alleviate, delay, reduce, reverse, improve or prevent at least one symptom of fibromyalgia.

The term "dual reuptake inhibitor" refers to a well-recognized class of antidepressant compounds that selectively inhibit reuptake of both norepinephrine and serotonin. "Norepinephrine-serotonin reuptake inhibitor" (NSRI) and "Serotonin-norepinephrine reuptake inhibitor" (SNRI) refer to subclasses of DRI's. DRI compounds that block the reuptake of norepinephrine preferentially are referred to as NSRI's, whereas those that preferentially block the reuptake of serotonin are referred to as SNRI's. Common DRI compounds include, but are not limited to, the SNRI's venlafaxine and duloxetine, and the NSRI's bicifadine and milnacipran.

NSRI compounds are described in detail in U.S. Pat. No. 6,602,911, the contents of which are hereby incorporated by reference in their entirety.

According to some embodiments, the present invention provides methods of long-term treatment of fibromyalgia syndrome in a patient comprising administering a DRI to a patient in need thereof for at least three months. In exemplary embodiments, the DRI compounds are NSRI's.

In other exemplary embodiments, the NSRI is milnacipran. In some embodiments, milnacipran may be administered as a hydrochloride salt: Z-2-aminomethyl-1-phenyl-N,N-diethyl-cyclopropanecarboxamide hydrochloride (chemical formula $C_{15}H_{23}ClN_2O$). In other embodiments, milnacipran may be administered as a mixture of the dextro- and levrogyral enantiomers, e.g., as a mixture that includes more of one enantiomer or as a racemic mixture. In some embodiments, milnacipran may be administered in an enantiomerically pure form (e.g., as the pure dextro- or pure levrogyral enantiomer). Unless otherwise indicated, milnacipran can include all stereoisomeric forms, mixtures of stereoisomeric forms, diastereomeric forms, and pharmaceutically acceptable salts thereof, including both enantiomerically pure forms of milnacipran as well as mixtures of milnacipran enantiomers. Methods for separating and isolating the dextro- and levrogyral enantiomers of milnacipran and other NE 5-HT SNRI compounds are well-known (see, e.g., Grard et al., 2000, Electrophoresis 2000 21:3028-3034).

Pharmaceutical compositions suitable for use in the present invention include compositions wherein the active ingredient is contained in a therapeutically or prophylactically effective amount, i.e., in an amount effective to achieve therapeutic or prophylactic benefit for the long-term treatment of FMS and its symptoms. Determination of an effective amount is well within the capabilities of those skilled in the art, especially in light of the disclosure herein.

Therapeutic amounts of DRI compounds typically range from about 1 μg to 1 gm/day. The amount of the DRI compound administered to practice the methods of the invention will, of course, be dependent on the DRI, the subject being treated, the severity of the affliction, and the manner of administration. See, e.g., U.S. application Ser. No. 10/678,767, the contents of which are hereby incorporated by reference in its entirety.

For example, therapeutically effective amounts can be determined from human data of DRI compounds used to treat depression. The therapeutically effective amount may be the same amount administered to treat depression or can be an amount higher or lower than the amount administered to treat depression. For example, the amount of milnacipran administered to treat depression may be in the range of about 50 mg to about 400 mg/day. Thus, about 50 mg to about 400 mg/day of milnacipran may be used for the long-term treatment of FMS and its symptoms. Dosages lower than about 50 mg/day of milnacipran may also be used for the long-term treatment of FMS and its symptoms. For example, for the treatment of FMS, CFS, or pain with milnacipran the dosage range is typically from 25 mg-400 mg/day, more typically from 100 mg-250 mg/day. The dosage may be administered once per day or several or multiple times per day.

Therapeutically effective amounts for use in humans can also be determined from animal models. For example, a dose for humans can be formulated to achieve circulating concentration that has been found to be effective in animals. Useful animal models of pain are well known in the art. For example, models of neuropathic pain are described in Zeltser et al., 2000, Pain 89:19-24; Bennett et al., 1988, Pain 33:87-107; Seltzer et al., 1990, Pain 43:205-218; Kim et al., 1992, pain using complete Freund's adjuvant is described in Jasmin et al., 1998, Pain 75: 367-382. The stress-induced hyperalgesia model described in Quintero et al., 2000, Pharmacology, Biochemistry and Behavior 67:449-458 may be used as an animal model of FMS and CFS.

The route of administration of the pharmaceutical compositions of the present invention may be, for example, oral, enteral, intravenous, and transmucosal (e.g., rectal). A preferred route of administration is oral. Pharmaceutical compositions suitable for oral administration can be in the form of tablets, capsules, pills, lozenges, powders or granules, or solutions or dispersions in a liquid. Each form will comprise a predetermined amount of a compound of the invention as an active ingredient. The compositions may be prepared as a tablet employing any pharmaceutical excipient known in the art for that purpose, and conventionally used for the preparation of solid pharmaceutical compositions. The examples of such excipients include, but are not limited to, starch, lactose, microcrystalline cellulose, magnesium stearate. Binders, such as polyvinylpyrrolidone, may also be used in the compositions of the present invention. Furthermore, an active compound can be formulated as controlled-release preparation, such as tablets comprising a hydrophilic or hydrophobic matrix.

The pharmaceutical compositions of the present invention may be in the form of capsules formulated using conventional procedures, for example by incorporation of a mixture of an active compound and excipients into a hard gelatin capsule. Alternatively, a semi-solid matrix of an active compound and high molecular weight polyethylene glycol may be formed and filled into hard gelatin capsules, or soft gelatin capsules may be filled with a solution of an active compound in polyethylene glycol or dispersion thereof in edible oil. Powder forms for reconstitution before use (for example lyophilized powders) are also contemplated. Alternatively, oily vehicles that may be used as injectable formulations may be used as well.

Liquid forms for parenteral administration may also be formulated for administration by injection or continuous infusion. Accepted routes of administration by injection are intravenous, intraperitoneal, intramuscular and subcutaneous. A typical composition for intravenous injection comprises a sterile isotonic aqueous solution or dispersion, including, for example, an active compound and dextrose or sodium chloride. Other examples of suitable excipients are lactated Ringer solution for injections, lactated Ringer solution for injections with dextrose, Normosol-M with dextrose, acylated Ringer solution for injections. The injection formulation can optionally include co-solvents (e.g., polyethylene glycol), chelating agents (e.g., ethylenediaminotetraacetic acid), stabilizing agents (e.g., cyclodextrin) and/or antioxidants (e.g., sodium pyrosulfate).

According to some embodiments, the DRI may be administered adjunctively with other active compounds for the long-term treatment of fibromyalgia syndrome. For example, active compounds that may be administered include antidepressants, analgesics, muscle relaxants, anorectics, stimulants, antiepileptic drugs, beta blockers, and sedative/hypnotics. Some examples of compounds that may be adjunctively administered with the DRI include, but are not limited to, modafinil, gabapentin, pregabalin, XP13512, pramipexole, 1-DOPA, amphetamine, tizanidine, clonidine, tramadol, morphine, tricyclic antidepressants, codeine, cambamazepine, sibutramine, valium, trazodone, caffeine, nicergoline, bifemelane, propranolol, atenolol, and combinations thereof. In an exemplary embodiment, the DRI may be milnacipran and may be adjunctively administered with an alpha-2-delta ligand such as, for example, pregabalin.

As used herein, adjunctive administration includes simultaneous administration of the compounds in the same dosage form, simultaneous administration in separate dosage forms, and separate administration of the compounds. For example, milnacipran may be simultaneously administered with valium, wherein both milnacipran and valium are formulated together in the same tablet. Alternatively, milnacipran may be simultaneously administered with valium, wherein both the milnacipran and valium are present in two separate tablets. In another alternative, milnacipran may be administered first followed by the administration of valium, or vice versa.

Milnacipran monotherapy for the treatment of fibromyalgia has been previously described in a Phase II trial of 125 fibromyalgia patients. See, e.g., U.S. application Ser. No. 10/678,767, the contents of which are hereby incorporated by reference in its entirety. In this study, milnacipran was administered once or twice daily in a dosage escalation regimen to a maximum dose of 200 mg/day. The study showed that milnacipran provided effective acute (short-term) therapy for symptoms of FMS. In particular, twice-daily (BID) and once-daily (QD) dosing of milnacipran were approximately equally effective on fatigue, mood, global wellness, and function. Twice-daily dosing was better tolerated than QD dosing, and was more effective in treating pain than QD dosing. The patient global impression of change (PGIC) outcome measure showed that over 70% of completers in both milnacipran treatment groups reported an improvement in their overall status, while only 10% reported worsening. In contrast, 40% of the placebo patients who completed the trial rated themselves as worse at endpoint. The differences between placebo and milnacipran on the PGIC were statistically significant, both in terms of a comparison of mean endpoint scores, as well as on a binary improved/not-improved basis.

Milnacipran was well-tolerated in this Phase II study. There were no deaths or serious adverse events (AEs) associated with milnacipran treatment, and the majority of AEs reported were rated as mild or moderate in severity. The most frequently reported AE was nausea, reported (one or more times) by 33% of milnacipran-treated patients; all other AES were reported in less than 9% of milnacipran-treated patients. The higher incidence of nausea, abdominal pain, headache and certain other AEs in the 200 mg QD treatment group suggests that larger doses taken once daily are not as well tolerated as smaller divided doses given twice a day. The reporting of dizziness, postural dizziness, hot flushes (and flushing), and palpitations was also greater in the QD treatment group, suggesting that peak drug level may be a significant factor in the generation of certain adverse effects.

Consistent with previous trial results, 7% of patients experienced mild increases in ALT and/or AST ($\leq 2$ times the upper limit of normal), without concomitant increases in bilirubin or alkaline phosphatase. Elevation in hepatic enzymes resulted in adverse events in only 2% of milnacipran-treated patients (i.e., 2 out of 7 patients with enzyme elevations reported the adverse event of "elevation in SGOT" or "elevation in SGPT").

A 4 to 8 beats-per-minute increase in mean heart rate was noted in milnacipran-treated patients, which was consistent with previous milnacipran trial results. Mean systolic and diastolic blood pressure among the milnacipran treatment groups showed only slight increases, ranging from 1.5 to 3.4 mmHg for supine systolic pressures (−1.1 to 2.7 mmHg in the placebo group), and 2.6 to 3.7 mmHg for supine diastolic pressures (−3.5 to 1.2 mmHg in the placebo group). Two (2%)

milnacipran BID-treated patients reported an exacerbation of hypertension; both patients had pre-existing hypertension and were receiving antihypertensive drug therapy. One patient withdrew early from the trial due to an exacerbation of hypertension.

The potential for treatment-related orthostatic effects was also documented during previous trials, and 6 (6%) of milnacipran-treated patients during the FMS trial reported the adverse event of orthostatic/postural dizziness, with one patient discontinuing early due to moderate postural dizziness. Vital sign data revealed that 4% of placebo patients and 7% of milnacipran patients experienced one or more visits with a decrease of 20 mm Hg or more in systolic blood pressure after standing erect for one minute.

Thus, the Phase II trial showed that treatment with milnacipran was an effective acute (short-term) therapy for the symptom of pain in FMS, and milnacipran dosed either once or twice daily had measurable beneficial effects on a wide range of symptoms of FMS, including fatigue (measured on the FIQ), pain (multiple measures), quality of life (multiple measures), and, potentially, mood (Beck instrument).

It has not been previously shown that milnacipran, or any other active agent, is effective for the long-term (greater than three months) treatment of FMS and its symptoms. The clinical study described in Example 1 below provides the first, and surprising, report of effective long-term treatment of FMS using a NSRI.

The following examples are merely illustrative of the present invention and should not be construed as limiting the scope of the invention in any way as many variations and equivalents that are encompassed by the present invention will become apparent to those skilled in the art upon reading the present disclosure.

EXAMPLES

Example 1

A Multi-Center Double-Blind, Randomized, Placebo-Controlled Study of Milnacipran for the Treatment of Fibromyalgia The primary objective of this study was to demonstrate safety and efficacy, both clinical and statistical, of milnacipran in the treatment of the fibromyalgia syndrome. The primary outcome was a composite responder analysis assessing response rate at weeks 14 and 15, and the secondary analysis assessed response rate at weeks 26 and 27.

Other objectives of this study were to:

1. compare statistical and clinical efficacy of 100 mg/day and 200 mg/day milnacipran in the treatment of the fibromyalgia syndrome based on each component of the composite responder analysis, as well as on a number of additional secondary endpoints including fatigue, sleep, mood and cognition; and 2. establish and compare the safety profiles of 100 and 200 mg milnacipran daily in patients with FMS.

Methodology

This was a multi-center, randomized, double-blinded, placebo-controlled three-arm study, which enrolled 888 patients who met the 1990 ACR criteria for fibromyalgia syndrome as well as the more detailed admission criteria outlined in the protocol.

Patients recorded baseline symptoms for the first two weeks after washing off anti-depressants, benzodiazepines, and certain other drugs that could potentially interfere with efficacy measurements.

Patients were randomized to receive placebo, 100 mg/day milnacipran, or 200 mg/day milnacipran in a ratio of a 1:1:2. All randomized medications (placebo and milnacipran) were administered in a split-dose (BID) fashion. The doses were administered in a dose escalation regimen as outlined below:
Step 1: 12.5 mg 1 day (12.5 mg pm)
Step 2: 25 mg 2 days (12.5 mg am, 12.5 mg pm)
Step 3: 50 mg 4 days (25 mg am, 25 mg pm)
Step 4: 100 mg 7 days (50 mg am, 50 mg pm)
Step 5: 200 mg 7 days (100 mg am, 100 mg pm).

All patients were scheduled to receive a total of 24 weeks of milnacipran or placebo after the 3 weeks of dose escalation steps, for a total of 27 weeks of milnacipran or placebo exposure.

Patients were required to complete electronic diary, as well as additional paper assessments as described in the schedule of study assessments.

Adverse event, physical examination, concomitant medication, vital sign and clinical laboratory data were collected as detailed in the schedule of study assessments.

Patients who successfully completed this double blind trial were eligible to participate in an open label trial for 15 to 28 additional weeks of therapy.

A timeline of the study is provided in FIG. 1.
Assessments
Safety:

Safety of milnacipran was assessed by analyzing the frequency and intensity of adverse events, changes in vital signs, as well as changes in physical examination and clinical laboratory data collected during the study period.

Efficacy:

In addition to the daily completion of a proprietary electronic patient diary, the following assessments were obtained:

a. Primary Variables: patient global impression of change (PGIC) and the Fibromyalgia Impact Questionnaire (FIQ);

b. Psychological Screening at baseline: M.I.N.I.;

c. Miscellaneous status assessments: periodically, as described in the schedule of evaluations: BDI, sleep quality scale, and the ASEX; and d. FMS Status Assessments: Patient pain 24 hour and 7 day recall VAS, the SF-36, Multiple Ability Self-report Questionnaire (MASQ, cognitive function), the Multidimensional Health Assessment Questionnaire (MDHAQ) and the Multidimensional Fatigue Inventory (MFI). Diary assessments include current pain (morning, random daily, and evening reports); daily recall pain (morning report); medications taken (evening report); overall pain past week (weekly report), overall fatigue in the last week (weekly report), and the extent that pain kept the patient from caring for themselves (weekly report).

The primary endpoint of this study was a composite responder analysis implementing analysis of three domains of interest, evaluated at 24 weeks as the primary analysis, and 12 weeks as the secondary analysis. The domains measured were:

1) pain (measured by an electronic diary as a daily recall pain score, calculated to weekly average scores);

2) patient global (measured by the PGIC, 1-7 scale); and 3) physical function (measured by the FIQ-PF).

For the primary analysis, the pain domain score was determined by a calculation that compared the average of treatment weeks 14 and 15 to the two baseline weeks, and treatment weeks 26 and 27 vs. baseline for the secondary analysis. The last observation was carried forward if neither the week 14 nor week 15 (or week 26/27) patient self-reported pain score is available to compare to the baseline value.

The binary response rate for placebo (based on the composite endpoint) in this study was expected to be in the range of 10-13%, with a milnacipran response rate in the active arm(s) expected in the 27-29% range on an ITT/LOCF basis. Based on these response rate assumptions, 125 patients randomized per arm (250 for high dose group) has been calculated to be the maximum sample size required (90% power). Secondary analyses included total area under the curve of pain intensity, and patient-reported weekly pain recall at the clinic visits as well as the FMS status assessments, and QOL measures.

Results:

A responder was defined as a subject who experienced a greater than 30% reduction in pain from baseline and improvement on the PGIC.

At three months, the percentage of responders was: 35.44% (56/158) in the placebo group; 53.33% (72/135) (p=0.001) in the milnacipran 100 mg/day group; and 55.00% (143/260) (p<0.001) in the milnacipran 200 mg/day group. At six months, the percentage of responders was: 32.86% (46/140) in the placebo group; 49.59% (60/121) (p=0.002) in the milnacipran 100 mg/day group; and 51.74% (119/230) (p<0.001) in the milnacipran 200 mg/day group. See Table 1 for a summary of the results in the Intent-to-Treat Population and Table 2 for a summary of the Last Observation Carried Forward (LOCF), Baseline Observation Carried Forward (BOCF) and study completer (OC) populations. LOCF is an analysis in which observations are carried forward to the last time point for patients who dropped out. The LOCF analysis treats the carried-forward data as observed data at the last time point. BOCF is an analysis that requires the patient remain active in the trial to be evaluated for response. If a patient withdraws from the trial for any reason they are classed as a non-responder irregardless of their pain and global scores at the time of withdrawal.

TABLE 1

Analysis of Responders for the Treatment of the Pain of Fibromyalgia during Treatment Weeks 14-15 and 26-27 (Observed Cases) Intent-to-Treat Population

| | Statistic | Placebo (N = 223) | Milnacipran 100 mg (N = 224) | Milnacipran 200 mg (N = 441) |
|---|---|---|---|---|
| Baseline pain | n | 223 | 224 | 441 |
| | mean | 68.37 | 68.32 | 69.41 |
| | SD | 11.98 | 11.54 | 11.85 |
| | SEM | 0.80 | 0.77 | 0.56 |
| | median | 66.5 | 67.9 | 69.1 |
| | min, max | 50, 100 | 41, 100 | 47, 99 |
| Treatment weeks 14-15 | n | 158 | 135 | 260 |
| | m (% = m/n) | 56 (35.44) | 72 (53.33) | 143 (55.00) |
| | odds ratio | | 2.10 | 2.20 |
| | 95% CI | | (1.31, 3.36) | (1.46, 3.31) |
| | p-value | | 0.002 | <0.001 |
| Treatment weeks 26-27 | n | 140 | 121 | 230 |
| | m (% = m/n) | 46 (32.86) | 60 (49.59) | 119 (51.74) |
| | odds ratio | | 1.96 | 2.20 |
| | 95% CI | | (1.18, 3.26) | (1.42, 3.41) |
| | p-value | | 0.009 | <0.001 |

TABLE 2

Summary of Composite Responder Rate - FMS031

| | Pain Composite Resp | | | | | |
|---|---|---|---|---|---|---|
| | 3 month | | | 6 month | | |
| | pbo N = 223 | 100 mg N = 224 | 200 mg N = 441 | pbo N = 223 | 100 mg N = 224 | 200 mg N = 441 |
| Primary Analysis (LOCF) | 27.8% | 33.5% p* = 0.187 | 34.9% p* = 0.058 | 25.1% | 30.8% p* = 0.197 ap* = 0.393 | 32.2% p* = 0.053 ap* = 0.105 |
| Sensitivity Analysis I (BOCF) | 25.1% | 32.1% p* = 0.094 | 32.4% p* = 0.048 | 20.6% | 26.8% p* = 0.167 ap* = 0.334 | 27.0% p* = 0.067 ap* = 0.133 |
| Sensitivity Analysis II | 25.56% | 32.% p* = 0.113 | 32.7% p* = 0.056 | 21.5% | 27.2% p* = 0.197 ap* = 0.394 | 28.6% p* = 0.048 ap* = 0.095 |
| Sensitivity Analysis III | 25.1% | 32.1% p* = 0.094 | 32.4% p* = 0.048 | 22.9% | 29.5% p* = 0.120 ap* = 0.241 | 29.9% p* = 0.051 ap* = 0.102 |
| OC Analysis | n* = 158 35.4% | n = 135 53.3% p* = 0.002 | n = 260 55.0% p* < 0.001 | n = 140 32.9% | n = 121 49.6% p* = 0.009 | n = 230 51.7% p* < 0.001 |

Summary of Individual Component Responder Rate - FMS031

| | Pain Composite Resp, 3 month | | | Pain Composite Resp, 6 month | | |
|---|---|---|---|---|---|---|
| | pbo | 100 mg | 200 mg | pbo | 100 mg | 200 mg |
| Primary Analysis (LOCF) | 27.8% | 33.5% p* = 0.187 | 34.9% p* = 0.058 | 25.1% | 30.8% p* = 0.197 ap* = 0.393 | 32.2% p* = 0.053 ap* = 0.105 |
| Pain (LOCF) | 31.4% | 35.7% p = 0.321 | 38.3% p = 0.068 | 28.7% | 35.7% p = 0.110 | 35.4% p = 0.072 |
| PGIC (LOCF) | 47.1% | 54.0% p = 0.143 | 50.6% p = 0.397 | 46.2% | 49.6% p = 0.476 | 49.9% p = 0.368 |

*p-value: nominal p-value.
ap = adjusted p-value at Step 2 for Hochberg's procedure (only valid if p-value is =<0.05 for 3-month pain for 200 mg compared to placebo at Step 1).
n = number of patients having adequate date for OC analysis (completers of landmark endpoint with observed values for responder assessment).

Figure 2:
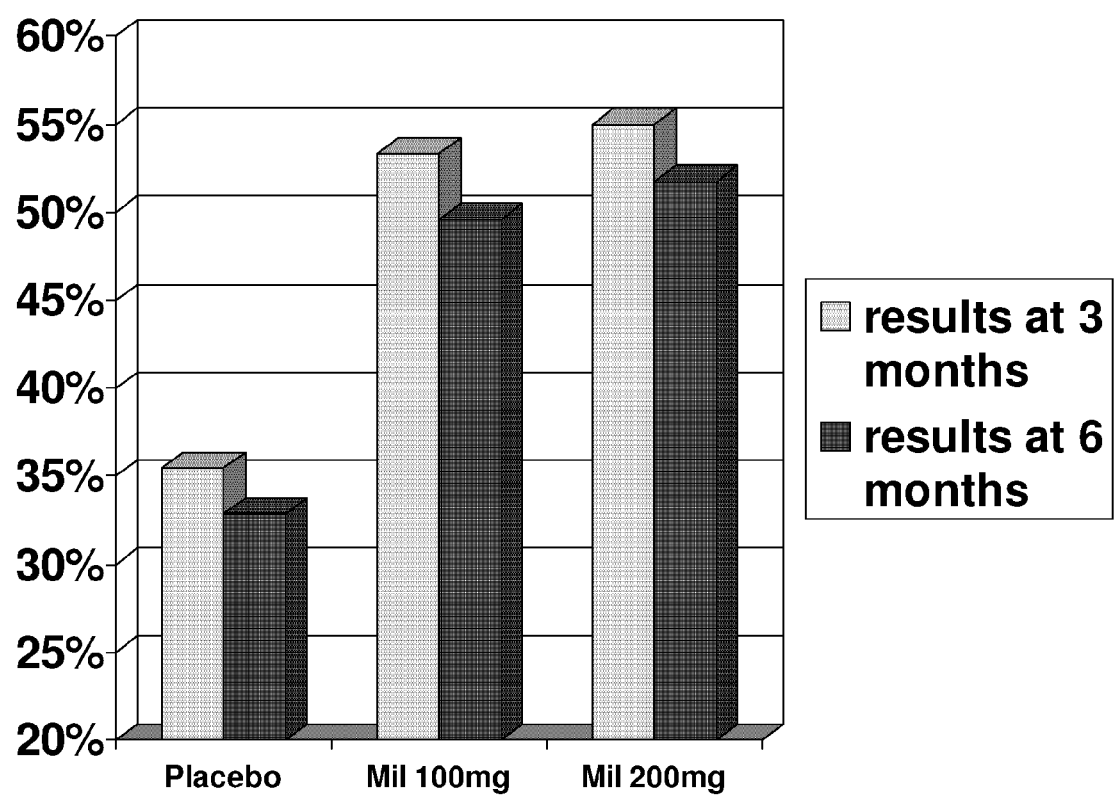
FIG. 2 is a bar graph which illustrates the percentage of responders at 3 months and 6 months for the placebo, milnacipran 100 mg/day and milnacipran 200 mg/day groups described in Example 1.

These results surprising establish that continued administration of milnacipran (e.g., daily administration for at least three months) to subjects suffering from fibromyalgia provides long-term (at least three months) relief from fibromyalgia and its symptoms. Further, these results surprisingly establish that continued administration of low dose milnacipran (e.g., 100 mg/day) is almost as effective as continued administration of high dose milnacipran (e.g., 200 mg/day) for the long-term treatment of fibromyalgia and its symptoms. FIG. 2.

While the invention has been depicted and described by reference to exemplary embodiments of the invention, such a reference does not imply a limitation on the invention, and no such limitation is to be inferred. The invention is capable of considerable modification, alteration, and equivalents in form and function, as will occur to those ordinarily skilled in the pertinent arts having the benefit of this disclosure. The depicted and described embodiments of the invention are exemplary only, and are not exhaustive of the scope of the invention. Consequently, the invention is intended to be limited only by the spirit and scope of the appended claims, giving full cognizance to equivalence in all respects. All references cited herein are hereby incorporated by reference in their entirety.

The invention claimed is:

1. A method of treating fibromyalgia in a patient suffering from fibromyalgia comprising administering milnacipran, or a pharmaceutically acceptable salt thereof, to the patient according to the following schedule:
   a) administering 12.5 mg milnacipran/day to the patient for 1 day; then
   b) administering 25 mg milnacipran/day to the patient for 2 days; then
   c) administering 50 mg milnacipran/day to the patient for 4 days; then
   d) administering 100 mg milnacipran/day.

2. The method of claim 1, wherein the milnacipran or a salt thereof is administered in a tablet dosage form.

3. The method of claim 2, wherein the tablet dosage form comprises an amount of milnacipran selected from 12.5 mg, 25 mg, 50 mg, or 100 mg.

4. The method of claim 1, wherein the milnacipran in steps b) to d) is administered twice daily.

5. The method of claim 1, wherein the milnacipran in step b) is administered as a 12.5 mg dosage two times per day.

6. The method of claim 1, wherein the milnacipran in step c) is administered as a 25 mg dosage two times per day.

7. The method of claim 1, wherein the milnacipran in step d) is administered as a 50 mg dosage two times per day.

* * * * *